US00PP16037P2

(12) United States Plant Patent
Gossett

(10) Patent No.: US PP16,037 P2
(45) Date of Patent: Oct. 11, 2005

(54) ***TRICYRTIS* PLANT NAMED 'MOONLIGHT TREASURE'**

(50) Latin Name: ***Tricyrtis nana*×*Tricyrtis ohsumiensis***
Varietal Denomination: Moonlight Treasure

(75) Inventor: Gary J. Gossett, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 32 days.

(21) Appl. No.: 10/872,287

(22) Filed: Jun. 18, 2004

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—Annette H Para
(74) *Attorney, Agent, or Firm*—Klarquist Sparkman, LLP

(57) ABSTRACT

A new and distinct hybrid *Tricyrtis* plant characterized by its compact habit, buttery yellow flower color, and heavy textured, deep green, mottled leaves.

1 Drawing Sheet

Botanical classification: *Tricyrtis nana*×*Tricyrtis ohsumiensis.*
Variety denomination: 'Moonlight Treasure'.

BACKGROUND OF THE INVENTION

The present invention relates to a new and distinct interspecific hybrid of the genus *Tricyrtis*, and given the cultivar name is 'Moonlight Treasure' *Tricyrtis* is in the family Liliaceae. The plant is an interspecific hybrid between *Tricyrtis nana* (unpatented, seed parent) and *Tricyrtis ohsumiensis* (unpatented, pollen parent).

SUMMARY OF THE INVENTION

This new cultivar unique and characterized by:

1. Upright, densely growing clumping habit.
2. Thick-textured, mottled leaves.
3. Large, speckled creamy yellow flowers at terminal and every leaf axil in clusters of 1 to 5 (usually 4).

This new cultivar has been reproduced only by asexual propagation (division and tissue culture). Each of the progeny exhibits identical characteristics to the original plant. Asexual propagation by tissue culture using standard micropropagation techniques with lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows a two year old *Tricyrtis* 'Moonlight Treasure' growing in a one gallon container in the shade house in Canby, Oreg.

DETAILED PLANT DESCRIPTION

The following is a detailed description of the new *Tricyrtis* cultivar based on observations of a three year old specimen grown in a one gallon pot in the shade house in Canby, Oreg. The color descriptions are all based on The Royal Horticultural Society Colour Chart.

Botanical classification: *Tricyrtis nana*×*Tricyrtis ohsumiensis.*
Variety denomination: 'Moonlight Treasure'.

Plant:
- *Type.*—Herbaceous perennial.
- *Hardiness.*—USDA Zones 6 to 9.
- *Size.*—42 cm. wide and 35 cm. tall.
- *Form.*—With short rhizomes forming a compact clump.

Stem:
- *Type.*—Unbranched stems, caulescent, erect.
- *Size.*—23 to 30 cm long and 0.5 cm wide with swollen nodes.
- *Surface.*—Sparsely pubescent on young growth.
- *Stem number.*—19.
- *Number of leaves per stem.*—5 to 11.
- *Color.*—Yellow Green 145A.

*Leaf:*
- *Type.*—Simple.
- *Shape.*—Elliptic to ovate.
- *Arrangement.*—*Alternate.*
- *Blade length.*—Grows to 17.5 cm.
- *Blade width.*—Grows to 7.5 cm.
- *Margins.*—Entire.
- *Apex.*—Cuspidate.
- *Base.*—Clasping.
- *Texture.*—Leathery, waxy.
- *Venation.*—Parallel.
- *Vestiture.*—Glabrous.
- *Color.*—Light green mottled dark green. Leaves become progressively darker and less spotted, more mottled going down the stem. Topside: Green 137 C spotted Green 139A to Green 137C almost completely mottled with Green 139A except at the base of the leaf. Bottom side: Yellow Green 137C.

Inflorescence:
- *Type.*—Axillary.
- *Number of flowers per stem.*—41 on a 30 cm stem.
- *Number of flowers per cyme.*—1 to 5 (usually 4).
- *Pedicel.*—Length: Grows from 2 to 2.5 cm long. Texture: Pubescent. Color: Yellow Green 145C with a reddish blush where exposed to more light, Greyed Orange 177B.
- *Bloom time.*—September to October in Canby, Oreg.

Flower bud:

*Size.*—2.5 cm deep and 1 cm. wide.

*Shape.*—Oblong, wider near the top with 3 saccate spurs at the base.

*Vestiture.*—Pubescent.

*Color.*—Yellow 4C with Yellow Green 144A tips.

Flower:

*Type.*—Actinomorphic, upfacing and flattish, with segments free.

*Shape.*—Starry, broadly campanulate.

*Size.*—Grows to 3 cm deep and 4.3 cm wide.

*Texture.*—Waxy.

*Vestiture.*—Glabrous inside, pubescent outside.

*Color.*—Buttery yellow, Yellow 6C, with small speckles of Greyed Red 178A all over the inside surface as well as in linear spots in a ring at the base. Back side is Yellow 6D with spotting visible.

*Tepals.*—Number — 6. Shape — Oblong. Inner tepals — 3 cm long and 1 cm wide with a retuse tip. Outer tepals — 2.8 cm long and 0.9 cm wide with a mucronate tip and a saccate spur at the base, reflex slightly.

*Pistil.*—2.2 cm. long.

*Stigma.*—3-parted, bifid at the tips, glandular, Yellow 13B with some spotting of Greyed Red 187A.

*Filaments.*—2.4 cm long, almost white, Yellow 4C.

*Anthers.*—Brown, Greyed Orange 177B.

*Pollen color.*—Yellow 4C.

*Fragrance.*—None.

Fruit:

*Type.*—Capsule.

*Size.*—2.2 cm long and 1.2 cm wide.

*Shape.*—Narrowly oblong, 3 angled.

*Color.*—Yellow Green 144D.

Seed: None produced to date.

Pest and diseases: Snail and slugs are the main problems on *Tricyrtis.* This new cultivar has leathery waxy leaves and appears to be less appealing to slugs. No other problems have been observed on plant grown under commercial conditions in Canby, Oreg.

COMPARISONS TO SIMILAR *TRICYRTIS*

There are no similar *Tricyrtis* on the market.

Compared to the species *Tricyrtis nana*, the seed parent (unpatented), *Tricyrtis* 'Moonlight Treasure' is much taller, with rounder leaves, and a lighter ring at the flower center.

Compared to the species *Tricyrtis ohsumienis*, the pollen parent (unpatented), the new cultivar is shorter, more compact, with shorter internodes, the leaves have much more substance to them.

I claim:

1. A new and distinct hybrid *Tricyrtis* plant substantially as shown and described, characterized by its compact habit, buttery yellow flower color and heavy textured, deep green, mottled leaves.

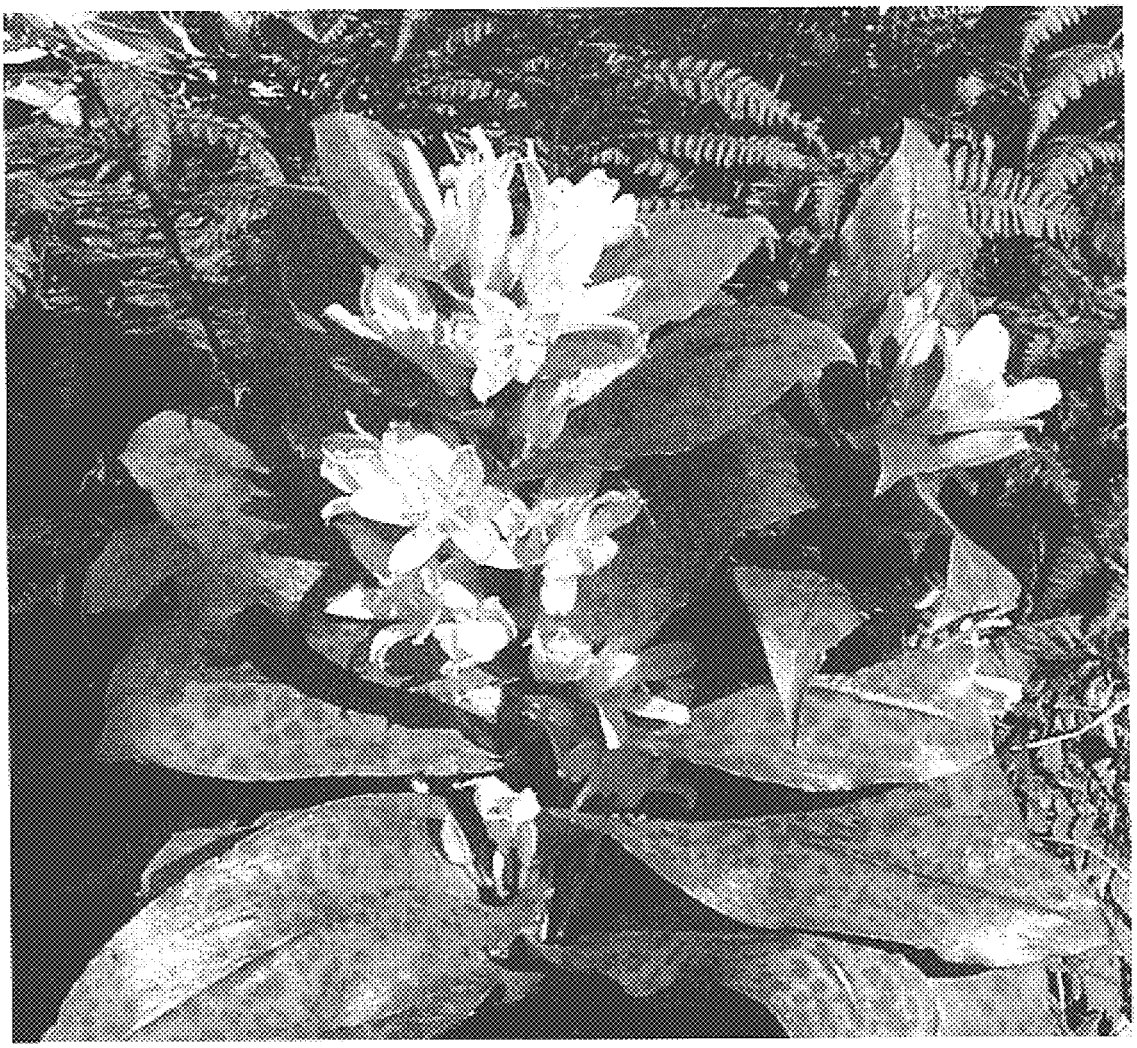

* * * * *